United States Patent [19]
Gordon et al.

[11] 4,406,887
[45] Sep. 27, 1983

[54] METHOD FOR TREATING RESISTANT BACTERIA INCLUDING ANAEROBES

[75] Inventors: Maxwell Gordon, Syracuse; I. Jacob Pachter, Fayetteville, both of N.Y.

[73] Assignee: Bristol-Myers Company, New York, N.Y.

[21] Appl. No.: 310,346

[22] Filed: Oct. 13, 1981

[51] Int. Cl.³ .............................................. A61K 35/00
[52] U.S. Cl. .................................................... 424/114
[58] Field of Search ....................... 424/114, 271, 246

[56] References Cited

U.S. PATENT DOCUMENTS

| | | | |
|---|---|---|---|
| 4,234,579 | 11/1980 | Barth | 424/246 |
| 4,258,041 | 3/1981 | O'Callaghan et al. | 424/246 |
| 4,276,285 | 6/1981 | Barth | 424/114 |
| 4,297,345 | 10/1981 | Howarth | 424/114 |
| 4,301,149 | 11/1981 | Crowley | 424/114 |

FOREIGN PATENT DOCUMENTS 887173  7/1981  Belgium ............................ 424/114

OTHER PUBLICATIONS

Andrews et al., Antimicrobial Agents and Chemotherapy, May, 1980, pp. 884-889.
Gorbach, S. L., —J. Infect. Diseases 135, Supplement, pp. S2 and S3, 3/77.
Comber, K. R. et al. —20th Interscience Conference on Antimicrobial Agents and Chemotherapy, New Orleans, La., Abstract No. 609, 9/80.
R. J. Fass, ibid., Abstract No. 605, 9/80.
R. Wise et al. —Antimicrobial Agents & Chemotherapy 17, 884-889, 1980.
Gorbach, S. I. et al. —New England Journal of Medicine 290, 1289-1294, 1974.
Pauline K. W. Yu et al. —Antimicrobial Agents and Chemotherapy 20, 63-65, 1981.

Primary Examiner—Jerome D. Goldberg
Attorney, Agent, or Firm—Robert E. Carnahan

[57] ABSTRACT

Bacteroides which are uniformly resistant to ceftazidime fail to grow when exposed to 2β-chloromethyl-2α-methylpenam-3α-carboxylic acid (BL-P 2013), which itself is non-inhibitory, in combination with ceftazidime. Bacteroides infections are abated by treatment of the infected mammal with this combination of substances.

8 Claims, No Drawings

METHOD FOR TREATING RESISTANT BACTERIA INCLUDING ANAEROBES

FIELD OF THE INVENTION

The method of the present invention uses drug, bioaffecting and body treating compositions containing semi-synthetic heterocyclic active ingredients of the penicillin and cephalosporin series.

DESCRIPTION OF THE PRIOR ART

Anaerobes exist as normal flora in the oropharnyx, vagina, and intestine and are associated with 90 percent of intraabdominal abscesses, 95 percent of appendiceal abscesses, 75 percent of upper tract female pelvic infections, 90 percent of aspiration pneumonia, 95 percent of lung abscesses, and 85 percent of brain abscesses. Anaerobes of the genus Bacteroides and particularly *Bacteroides fragilis* are found in 70 percent of intraabdominal and pelvic infections (Gorbach, S. L., J. Infect. Diseases 135, Supplement, March, 1977 pp. S2 and S3).

Chemotherapeutic agents effective against *B. fragilis* are blighted by serious deficiencies. Clindamycin, the presently preferred antibiotic for the treatment of Bacteroides infection is compromised by the problem of pseudomembranous colitis which is sometimes fatal. Tetracycline and its congeners are relatively inactive against 30 to 50 percent of the strains of *B. fragilis* and intravenous treatment with large doses of the tetracyclines has serious liver, renal and intestinal complications. Chloramphenicol has a wide spectrum of activity against *B. fragilis* but is plagued by hematologic complications. Carbenicillin once believed to be widely effective against *B. fragilis* now appears to be roughly equivalent to penicillin G and is only effective against about 10 to 20 percent of the strains of *B. fragilis* (Gorbach, S. L., op. cit.).

A mixture of amoxicillin and clavulanic acid has recently demonstrated good activity against experimentally induced *Bacteroides fragilis* infection (Comber, K. R. et al., 20th Interscience Conference on Antimicrobial Agents and Chemotherapy, New Orleans, La., Abstract No. 609 (Sept., 1980)). Penicillanic acid-1,1-dioxide (CP-45,899), a β-lactamase inhibitor which is the subject of U.S. Pat. No. 4,234,579, is reported to be highly synergistic with ampicillin and sporadically synergistic with other antibiotics against *B. fragilis* (R. J. Fass, ibid., Abstract No. 605 (Sept., 1980)).

Ceftazidime, also referred to as GR 20263, is a new parenteral aminothiazolyl cephalosporin which has the advantages of stability to a wide range of β-lactamases, a broad antibacterial spectrum, and low toxicity. Ceftazidime, however, has low activity against *B. fragilis* and is believed to be ineffective in treating infections caused by that organism (Wise, R. et al., Antimicrobial Agents & Chemotherapy 17, 884–889 (1980)). Ceftazidime has the following structural formula and is the subject of U.S. Pat. No. 4,258,041 patented Mar. 24, 1981:

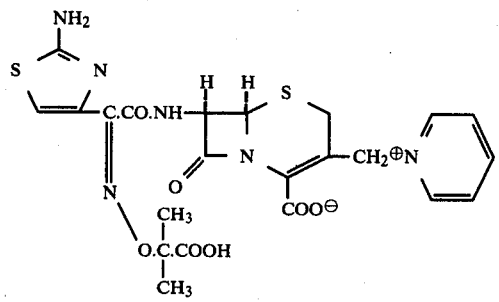

The term "ceftazidime" is intended to include not only the antibiotic having the foregoing structural formula but also its non-toxic salts such as the sodium salt and its non-toxic metabolically labile esters. Various salts and esters of the type contemplated are identified in the foregoing patent at column 4 beginning at line 46 and continuing to column 5 at line 20. The entire disclosure of U.S. Pat. No. 4,258,041 is incorporated herein by reference.

The β-lactamase inhibitor BL-P 2013 is an acid which with its pharmaceutically acceptable salts and physiologically hydrolyzable esters are the subject of Belgian Pat. No. 887,173. BL-P 2013 acid has the following structural formula:

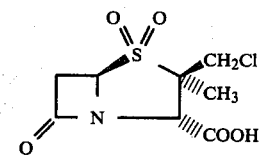

The term "BL-P 2013 compound" when used herein is intended to include the acid having the preceding formula, its pharmaceutically acceptable salts, and the physiologically hydrolyzable esters thereof.

The pharmaceutically acceptable salts referred to above include the non-toxic metallic salts such as the sodium, potassium, calcium, magnesium, and ammonium salts, and the substituted ammonium salts, e.g. salts of such non-toxic amines as trialkylamines (e.g. triethylamine), procaine, dibenzylamine, N-benzyl-β-phenethylamine, 1-ephenamine, N,N'-dibenzyl-ethylenediamine, dehydroabietylamine, N,N'-bis(dehydroabietyl)ethylenediamine, N-(lower)alkylpiperidine (e.g. N-ethylpiperidine) and other amines which have been used to form pharmaceutically acceptable salts of penicillins and cephalosporins. The most preferred salts are the alkali metal salts, i.e. the sodium and potassium salts, and the ammonium salt.

The terms "physiologically hydrolyzed esters" and "metabolically labile esters" refer to those pharmaceutically acceptable esters known in the art to hydrolyze to the free acid form in vivo. Examples of such esters include phenacyl, acetoxymethyl, pivaloyloxymethyl, α-acetoxyethyl, α-acetoxybenzyl, α-pivaloyloxyethyl, phthalidyl (3-phthalidyl), indanyl (5-indanyl), methoxymethyl, benzoyloxymethyl, α-ethylbutyryloxymethyl, propionyloxymethyl, valeryloxymethyl, isobutyryloxymethyl, and others with which medicinal chemists are familiar. The preferred esters are the acetoxymethyl, pivaloyloxymethyl, methoxymethyl, 3-phthalidyl, and 5-indanyl.

SUMMARY OF THE INVENTION

The present invention provides a method for the treatment of bacteroides infections which involves concurrent administration of the antibiotic ceftazidime with a BL-P 2013 compound. Ceftazidime is administered parenterally to a mammalian host having an infection caused by a bacteroides species and the BL-P 2013 compound is administered either parenterally or orally. Ceftazidime is administered in a well tolerated non-toxic dose which in itself is ineffective to inhibit the growth of the bacteroides organism. The BL-P 2013 compound is administered concurrently in a non-toxic physiologically acceptable dose of sufficient size to be effective with the ceftazidime to inhibit the growth of the bacteroides organism.

DETAILED DESCRIPTION OF THE INVENTION

The presence of bacteroides infection should be presumed and treatment according to the present invention commenced when the following criteria are met (Sweet, R. L., American Journal of Obstetrics and Gynecology 122, 891–901 (1975)).

1. Systemic infections complicating manipulations of the gastrointestinal tract or female pelvic organs.
2. Foul smelling exudates containing Gram negative bacilli which fail to grow on routine aerobic cultures.
3. Presence of gas within an abscess.
4. Presence of septic pelvic thrombophlebitis or septic emboli.
5. Failure to respond to the commonly used bactericidal antibiotics such as kanamycin, gentamicin, penicillin and cephalothin.
6. The presence of poorly stained Gram negative pleomorphic rods particularly when large numbers of organism are intracellular.

Such infections are frequently associated with damaged epithelial surfaces or mucous membranes. The term "bacteroides infection" as used herein is intended to apply to infections wherein a Bacteroides is isolated in pure or mixed culture from the infected zone. Certain infectious processes involve several strains of bacteria which behave in a cooperative fashion to produce an infection. Such conditions are also subject to treatment according to the present invention when a Bacteroides is a member of such a mixed culture. (Gorbach, S. I. et al., New England Journal of Medicine 290, 1289–94 (1974)).

The culturing and identification of anaerobes from clinical specimens require sophisticated methods and may require several days or even weeks. Treatment according to the present invention should not be delayed to await positive identification when a bacteroides infection is suspected or presumed. Empirical therapy should be commenced when the above criteria are observed. Treatment is continued as long as infection persists and for 10 days or more thereafter.

The dosage employed for adult human treatment with ceftazidime is preferably in the range of from 500 to 6,000 mg per day administered intravenously or intramuscularly. A dose is employed which is in itself ineffective to abate the infection, but which is well tolerated by the host and without toxic effect. Usually the daily dose is administered as several divided portions during each day of treatment.

BL-P 2013 is useful when given orally or parenterally concomitantly with ceftazidime. Parenteral dosage compositions containing both BL-P 2013 and ceftazidime may be employed. On a weight basis the dosage of BL-P 2013 is from 1/5 to 5 times, and preferably equal to, that of ceftazidime. As indicated they may be given either in admixture or concomitantly as separate dosage units. Parenteral administration includes intramuscular, subcutaneous, intraperitoneal, and intravenous administration.

A carrier or diluent is ordinarily used in administering the BL-P 2013 compound and ceftazidime and is chosen on the basis of the intended mode of administration. For example, when considering the oral mode of administration, the BL-P 2013 compound can be used in the form of tablets, capsules, lozenges, troches, powders, syrups, elixirs, aqueous solutions, and the like, in accordance with standard pharmaceutical practice. The proportional ratio of active ingredients to carrier will naturally depend on the chemical nature, solubility, stability and potency of the active ingredients, as well as the dosage contemplated. However, these pharmaceutical compositions will likely contain from about 5% to about 80% of carrier. In the case of tablets for oral use, carriers which are commonly used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols. When aqueous suspensions are required for oral use, the active ingredients are combined with emulsifying and suspending agents. If desired, certain sweetening and/or flavoring agents can be added.

For parenteral administration, which includes intramuscular, intraperitoneal, subcutaneous and intravenous use, sterile solutions of the active ingredients are usually prepared, and the pH of the solutions are suitably adjusted and buffered. For intravenous use, the total concentration of solutes should be preferably controlled to render the preparation substantially isotonic.

The prescribing physician will decide the dosage to be used in a human subject including the ratio of the dosage weight of BL-P 2013 compound and ceftazidime. The daily oral dosage of BL-P 2013 compound will normally be in the range of from 10 to about 200 milligrams per kilogram of body weight and the daily parenteral dosage will normally be in the range of about 10 to about 100 milligrams per kilogram of body weight. In some cases it may be necessary to use dosages outside these limits and these figures are to be considered illustrative only.

Biological Data

BL-P 2013 as the potassium salt was tested in vitro for synergism with ceftazidime as to the minimum inhibitory concentrations of the two substances alone and in combination on an equal weight basis against a variety of bacteria. Marked synergism was found with respect to various ceftazidime resistant strains of *Enterobacter cloacae, Clostridium perfringens, Enterobacter aerogenes, Clostridium freundii, Citrobacter species,* and *Morganella morganii*. Marginal synergism was seen in some instances with the two substances tested together as above against ceftazidime sensitive strains of these and other bacteria, but not against others. Importantly, of 16 *Bacteroides fragilis* strains tested, all were resistant to ceftazidime and all were inhibited by a 1:1 ceftazidime-BL-P 2013 combination. The results are given below:

TABLE 1

Antibacterial Activity of Ceftazidime Alone and in Combination with BL-P 2013 K Salt

| Organism | No. of Strains | BL-P 2013 (B) | A:B 1:1 | Ceftazidime (A) |
|---|---|---|---|---|
| S. aureus (p$^-$) | 9 | 100 | 7.4:7.4 | 8 |
| S. aureus (p$^+$) | 9 | 73 | 8:8 | 8 |
| E. aerogenes | 1 | >125 | 8.8$^c$ | 32 |
| E. cloacae | 1 | >125 | 8:8$^c$ | 63 |
| E. cloacae | 1 | >125 | 125:125 | >125 |
| Citrobacter sp. | 1 | 8 | 1:1 | 2 |
| C. freundii | 1 | >125 | 8:8$^c$ | 125 |
| S. marcescens | 2 | >125 | 2.8:2.8 | 4 |
| P. aeruginosa | 1 | >125 | 8:8 | 8 |
| P. aeruginosa | 6 | >125 | 4:4 | 4 |
| B. fragilis$^a$ | 12 | 21 | 1.8:1.8$^c$ | 29 |
| B. fragilis$^a$ | 4 | 25 | 5.7:5.7$^c$ | >125 |
| C. perfringens | 3 | >125 | 0.04:0.04 | 0.04 |
| C. perfringens | 3 | 89 | 0.25:0.25 | 0.7 |
| C. perfringens | 8 | >120 | 1.3:1.3 | 3.3 |

Run Nos. 1353, 1354 and 1359

$^a$Minimum inhibitory concentration (MIC) determined by the agar dilution method using 50× dilutions of 24 hour cultures as inocula dispensed by the Steer's inoculator. Assay medium composed of Brucella Agar plus 5% laked sheep blood and 10 mcg/ml vitamin K.
$^b$Geometric mean value where applicable. Anaerobe data based on 2 tests.
$^c$ marked synergism;
-- marginal synergism.

TABLE 2

Antibacterial Activity of Ceftazidime Alone and in Combination with BL-P 2013

| Organism | Number of Strains | Ceftazidime (A) | A:B 1:1 | BL-P 2013 (B) |
|---|---|---|---|---|
| Enterobacter aerogenes | 2 | 22.6 | 4:4 | >125 |
| | 3 | 1.3 | 1.3:1.3 | >125 |
| | 2 | 0.25 | 0.13:0.13 | >125 |
| Enterobacter cloacae | 2 | 44.9 | 8:8 | >125 |
| | 3 | 5.0 | 2.5:2.5 | >125 |
| | 1 | 1.0 | 0.25:0.25 | >125 |
| | 3 | 1.3 | 1.3:1.3 | >125 |
| Citrobacter species | 2 | 63 | 8:8 | >125 |
| | 1 | 1 | 0.5:0.5 | >125 |
| | 1 | 2 | 1:1 | 4 |
| | 3 | 1.3 | 1.3:1.3 | >125 |
| Serratia marcescens | 1 | >125 | 63:63 | >125 |
| | 1 | 16 | 8:8 | >125 |
| | 2 | 2 | 0.7:0.7 | >125 |
| | 1 | 1 | 0.5:0.5 | >125 |
| | 5 | 1.3 | 1.3:1.3 | >125 |
| Morganella morganii | 1 | 8 | 1:1 | >125 |
| | 1 | 1 | 0.13:0.13 | >125 |
| | 2 | 0.35 | 0.06:0.06 | >125 |
| | 4 | 0.063 | 0.03:0.03 | >125 |
| | 1 | 0.063 | 0.06:0.06 | >125 |
| Proteus vulgaris | 1 | 0.063 | 0.03:0.03 | >125 |
| | 4 | 0.063 | 0.06:0.06 | >125 |
| Providencia rettgeri | 5 | 1 | 0.5:0.5 | >125 |
| | 1 | 1 | 1:1 | >125 |
| | 3 | 0.13 | 0.16:0.16 | >125 |
| | 1 | 0.063 | 0.03:0.03 | >125 |
| Providencia stuartii | 1 | 1 | 2:2 | >125 |
| | 1 | 0.13 | 0.06:0.06 | >125 |
| | 27 | 0.24 | 0.24:0.24 | >125 |
| | 3 | 0.20 | 0.4:0.4 | >125 |

Run Nos. 1376, and 1377

$^a$Geometric mean MIC where applicable.
-- marginal synergism;
__ marked synergism.

Note: As a rule none of the strains of the above species showed an inoculum effect with ceftazidime within the range of $10^4$ to $2 \times 10^5$ CFUs.

TABLE 3

Antibacterial Activity of Ceftazidime Alone and in Combination with BL-P 2013

| Organism | No. of Strains | Ceftazidime | Ceftazidime: BL-P 2013 (1:1) | BL-P 2013 |
|---|---|---|---|---|
| S. aureus (P$^-$) | 9 | 8.6 | 7.1:7.1 | 96 |
| S. aureus (P$^+$) | 9 | 9.7 | 7.4:7.4 | 85 |
| E. aerogenes | 1 | 11.3 | 5.7:5.7 | >125 |
| E. cloacae | 1 | 63 | 8:8$^c$ | >125 |
| E. cloacae | 1 | >125 | >125:>125 | >125 |
| Citrobacter species | 1 | 2 | 1.4:1.4 | 4 |
| C. freundii | 1 | 63 | 8:8 | >125 |
| S. marcescens | 2 | 4 | 3.4:3.4 | >125 |
| P. aeruginosa | 7 | 4.9 | 4.9:4.9 | >125 |
| B. fragilis$^a$ | 16 | >32 | 2.7:2.7$^c$ | >32 |
| C. perfringens | 4 | 0.11 | 0.003:0.003$^c$ | 27 |
| C. perfringens | 6 | 0.1 | 0.003:0.003$^c$ | >32 |
| C. perfringens | 1 | 2 | 0.25:0.25$^c$ | >32 |
| C. perfringens | 2 | 5.7 | 4:4 | >32 |

Run Nos. 1332, 1333, 1334 and 1335

$^a$Minimum inhibitory concentration (MIC) determined by the agar dilution method using 50× dilutions of 24 hour cultures as inocula dispensed by the Steer's inoculator. Assay medium composed of Brucella Agar plus 5% laked sheep blood and 10 mcg/ml vitamin K.
$^b$Geometric mean MIC value where applicable.
$^c$-- marginal synergism,
__ marked synergism.

Operative blood concentrations of BL-P 2013 are produced in mice following oral administration of doses of 25 to 100 mg./kg. of body weight of the following BL-P 2013 compounds to mice.

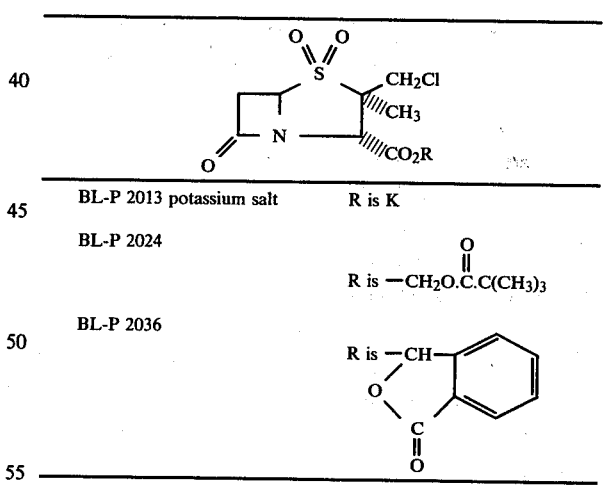

BL-P 2013 potassium salt — R is K

BL-P 2024 — R is $-CH_2O.\overset{O}{\underset{\|}{C}}.C(CH_3)_3$

BL-P 2036 — R is $-CH\underset{O}{\overset{O}{<}}\text{(phthalidyl)}$

Mice may be infected according to established technique with B. fragilis and PD$_{50}$ values (protective dose for 50% of the animals) determined employing various combinations of the foregoing substances with ceftazidime in various proportions.

| Injectible Compositions | |
|---|---|
| Ceftazidime | 500 mg. |
| BL-P 2013 K salt | 500 mg. |
| Sodium Carbonate | 47 mg. |

The foregoing materials, all having approximately the same particle size are dry-blended and then loaded into glass vial which is sterilized and sealed. This material is constituted for use by dissolution aseptically in from 4 to 10 ml. of water for injection.

What is claimed is:

1. A method for the treatment of a presumed bacteroides infection in a mammalian host which comprises parenteral treatment of said host with a non-toxic dose of 500 to 6000 mg. of ceftazidime per day and concurrently administering thereto a BL-P2013 compound selected from the group consisting of the acid having the formula:

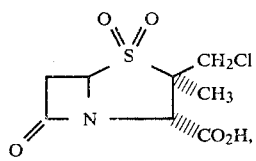

a pharmaceutically acceptable salt of said acid, and an ester of said acid selected from the group consisting of phenacyl, acetoxymethyl, pivaloyloxymethyl, α-acetoxyethyl, α-acetoxybenzyl, α-pivaloyloxyethyl, phthalidyl, indanyl, methoxymethyl, benzoyloxymethyl, α-ethylbutyryloxymethyl, propionyloxymethyl, valeryloxymethyl, and isobutyryloxymethyl the amount of said BL-P2013 compound being equal in weight to said dose of ceftazidime and effective with said dose of ceftazidime to inhibit the growth of said Bacteroides.

2. The method of claim 1 wherein said BL-P 2013 compound is administered parenterally.

3. The method of claim 1 wherein said ceftazidime and said BL-P 2013 compound are administered parenterally as a single dosage unit composition.

4. The method of claim 1 wherein said BL-P 2013 compound is administered orally.

5. The method of claims 2, 3, or 4 wherein said BL-P 2013 compound is the potassium salt of BL-P 2013.

6. The method of claim 4 wherein said BL-P 2013 compound has the following formula:

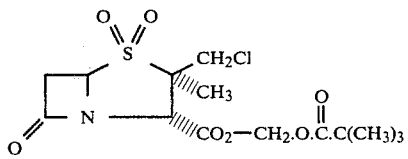

7. The method of claim 4 wherein said BL-P 2013 compound has the following formula:

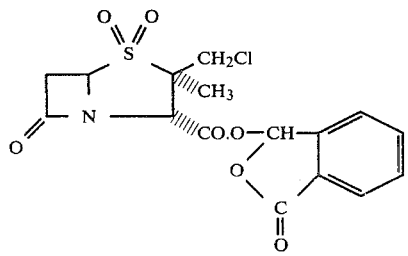

8. The method for the treatment of an infection in a mammalian host wherein said infection is caused by an organism selected from the group consisting of a ceftazidime resistant strain of *Enterobacter cloacae, Enterobacter aerogenes, Clostridium perfringens, Clostridium freundii,* Citrobacter species, *Morganella morganii,* Bacteroides species, and a mixture containing 2 or more of said organisms which comprises parenteral treatment of said host with a non-toxic dose of from 500 to 6000 mg. of ceftazidime per day and concurrently administering thereto a BL-P2013 compound selected from the group consisting of the acid having the formula:

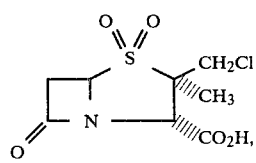

a pharmaceutically acceptable salt of said acid, and an ester of said acid selected from the group consisting of phenacyl, acetoxymethyl, pivaloyloxymethyl, α-acetoxyethyl, α-acetoxybenzyl, α-pivaloyloxyethyl, phthalidyl, indanyl, methoxymethyl, benzoyloxymethyl, α-ethylbutyryloxymethyl, propionyloxymethyl, valeryloxymethyl, and isobutyryloxymethyl the amount of said BL-P2013 compound being equal in weight to said dose of ceftazidime and effective with said dose of ceftazidime to inhibit the growth of said organism.

* * * * *